US010905866B2

(12) United States Patent
Tallarida et al.

(10) Patent No.: US 10,905,866 B2
(45) Date of Patent: Feb. 2, 2021

(54) DEVICES, SYSTEMS AND METHODS FOR REMOVAL AND REPLACEMENT OF A CATHETER FOR AN IMPLANTED ACCESS PORT

(71) Applicant: Versago Vascular Access, Inc., West Bridgewater, MA (US)

(72) Inventors: Steven J. Tallarida, Mansfield, MA (US); John M. Butziger, East Greenwich, RI (US); Richard P. Rodgers, Hudson, MA (US)

(73) Assignee: Versago Vascular Access, Inc., West Bridgewater, MA (US)

( * ) Notice: Subject to any disclaimer, the term of this patent is extended or adjusted under 35 U.S.C. 154(b) by 965 days.

(21) Appl. No.: 14/975,638

(22) Filed: Dec. 18, 2015

(65) Prior Publication Data
US 2016/0175575 A1   Jun. 23, 2016

Related U.S. Application Data

(60) Provisional application No. 62/093,769, filed on Dec. 18, 2014.

(51) Int. Cl.
*A61M 39/02* (2006.01)
*A61M 39/12* (2006.01)
(Continued)

(52) U.S. Cl.
CPC ........ *A61M 39/0208* (2013.01); *A61M 39/12* (2013.01); *A61M 25/04* (2013.01);
(Continued)

(58) Field of Classification Search
CPC ...... A61M 2025/0019; A61M 39/0208; A61M 2039/0205; A61M 1/3653;
(Continued)

(56) References Cited

U.S. PATENT DOCUMENTS 975,285 A    11/1910  Robertson
3,757,585 A   9/1973  Heller et al.
(Continued)

FOREIGN PATENT DOCUMENTS

EP   1680174   7/2006
EP   2403431   1/2012
(Continued)

OTHER PUBLICATIONS

PCT International Search Report dated Nov. 21, 2001 issued in PCT Application No. PCT/US01/13749, 4 pages.
(Continued)

*Primary Examiner* — Scott J Medway
(74) *Attorney, Agent, or Firm* — Grossman Tucker Perreault & Pfleger PLLC

(57) ABSTRACT

A medical device is provided which comprises an implantable vascular access port including a fluid passage operable to introduce fluid to a host and/or remove fluid from the host, the fluid passage accessible through a fluid passage access opening and at least a portion of the fluid passage defined by a needle configured to penetrate cutaneous tissue of the host; and an implantable vascular access catheter connectable with the vascular access port; wherein the vascular access catheter and the vascular access port are connectable to each other within the vascular access port.

22 Claims, 8 Drawing Sheets

(51) Int. Cl.
*A61M 5/142* (2006.01)
*A61M 25/04* (2006.01)

(52) U.S. Cl.
CPC .............. *A61M 2005/14284* (2013.01); *A61M 2039/0202* (2013.01); *A61M 2039/0205* (2013.01)

(58) Field of Classification Search
CPC ...... A61M 2039/0258; A61M 25/0017; A61M 39/0247; A61M 2025/0018; A61M 16/0463; A61M 25/00; A61M 39/04; A61M 5/158; A61M 2039/0235
USPC ............ 604/28, 247, 265, 267, 288.01, 508, 604/891.1
See application file for complete search history.

(56) References Cited

U.S. PATENT DOCUMENTS

| | | |
|---|---|---|
| 3,819,282 A | 6/1974 | Schultz |
| 4,096,896 A | 6/1978 | Engel |
| 4,181,132 A | 1/1980 | Parks |
| 4,190,040 A | 2/1980 | Schulte |
| 4,228,802 A | 10/1980 | Trott |
| 4,445,896 A | 5/1984 | Gianturco |
| 4,543,088 A | 9/1985 | Bootman et al. |
| 4,576,595 A | 3/1986 | Aas et al. |
| 4,673,394 A | 6/1987 | Fenton, Jr. et al. |
| 4,676,782 A * | 6/1987 | Yamamoto ........ A61M 39/0247 604/175 |
| 4,692,146 A | 9/1987 | Hilger |
| 4,710,167 A | 12/1987 | Lazorthes |
| 4,760,837 A | 8/1988 | Petit |
| 4,760,844 A | 8/1988 | Kyle |
| 4,781,680 A | 11/1988 | Redmond et al. |
| 4,802,885 A | 2/1989 | Weeks et al. |
| 4,840,615 A | 6/1989 | Hancock et al. |
| 4,892,518 A | 1/1990 | Cupp et al. |
| 4,904,241 A | 2/1990 | Bark |
| 4,919,653 A | 4/1990 | Martinez et al. |
| 4,929,236 A | 5/1990 | Sampson |
| 5,003,657 A | 4/1991 | Boiteau et al. |
| 5,006,115 A | 4/1991 | McDonald |
| 5,013,316 A | 5/1991 | Goble et al. |
| 5,041,098 A | 8/1991 | Loiterman et al. |
| 5,057,084 A | 10/1991 | Ensminger et al. |
| 5,084,015 A | 1/1992 | Moriuchi |
| 5,120,221 A | 6/1992 | Orenstein et al. |
| 5,137,529 A | 8/1992 | Watson et al. |
| 5,180,365 A | 1/1993 | Ensminger et al. |
| 5,203,771 A | 4/1993 | Melker et al. |
| 5,213,574 A | 5/1993 | Tucker |
| 5,215,530 A | 6/1993 | Hogan |
| 5,217,462 A | 6/1993 | Asnis et al. |
| 5,234,406 A | 8/1993 | Dransner et al. |
| 5,281,199 A | 1/1994 | Ensminger et al. |
| 5,295,658 A | 3/1994 | Atkinson et al. |
| 5,306,255 A | 4/1994 | Haindl |
| 5,318,545 A | 6/1994 | Tucker |
| 5,332,398 A | 7/1994 | Miller et al. |
| 5,337,756 A | 8/1994 | Barbier et al. |
| 5,338,398 A | 8/1994 | Szwejkowski et al. |
| 5,350,360 A | 9/1994 | Ensminger et al. |
| 5,352,204 A | 10/1994 | Ensminger |
| 5,360,407 A | 11/1994 | Leonard |
| 5,387,192 A | 2/1995 | Glantz et al. |
| 5,391,801 A | 2/1995 | Sato et al. |
| 5,399,168 A | 3/1995 | Wadsworth, Jr. et al. |
| 5,417,656 A | 5/1995 | Ensminger et al. |
| 5,423,334 A * | 6/1995 | Jordan ................. A61B 5/0031 128/899 |
| 5,476,460 A | 12/1995 | Montalvo |
| 5,498,265 A | 3/1996 | Asnis et al. |
| 5,520,643 A | 5/1996 | Ensminger et al. |
| 5,522,817 A | 6/1996 | Sander et al. |
| 5,527,278 A | 6/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,613,945 A | 3/1997 | Cai et al. |
| 5,637,088 A * | 6/1997 | Wenner ............. A61M 39/0208 604/93.01 |
| 5,643,267 A | 7/1997 | Hitomi et al. |
| 5,647,855 A | 7/1997 | Trooskin |
| 5,695,490 A | 12/1997 | Flaherty et al. |
| 5,702,413 A | 12/1997 | Lafontaine |
| 5,704,915 A | 1/1998 | Melsky et al. |
| 5,718,682 A | 2/1998 | Tucker |
| 5,718,692 A | 2/1998 | Schon et al. |
| 5,792,104 A | 8/1998 | Speckman et al. |
| 5,792,123 A | 8/1998 | Ensminger |
| 5,797,879 A | 8/1998 | DeCampli |
| 5,833,654 A | 11/1998 | Powers et al. |
| 5,836,935 A | 11/1998 | Ashton et al. |
| 5,843,069 A | 12/1998 | Butler et al. |
| 5,848,989 A | 12/1998 | Villani |
| 5,928,236 A | 7/1999 | Augagneur et al. |
| 5,931,801 A | 8/1999 | Burbank et al. |
| 5,951,512 A | 9/1999 | Dalton |
| 5,954,691 A | 9/1999 | Prosl |
| 5,989,206 A | 11/1999 | Prosl et al. |
| 6,007,516 A * | 12/1999 | Burbank ............. A61M 1/3653 251/149.7 |
| 6,030,397 A | 2/2000 | Monetti et al. |
| 6,039,712 A | 3/2000 | Fogarty et al. |
| 6,045,573 A | 4/2000 | Wenstrom, Jr. et al. |
| 6,048,343 A | 4/2000 | Mathis et al. |
| 6,056,751 A | 5/2000 | Fenton, Jr. |
| 6,113,572 A | 9/2000 | Gailey et al. |
| 6,139,565 A | 10/2000 | Stone et al. |
| 6,190,352 B1 | 2/2001 | Haarala et al. |
| 6,213,973 B1 | 4/2001 | Eliasen et al. |
| 6,413,260 B1 | 7/2002 | Berrevoets et al. |
| 6,478,783 B1 | 11/2002 | Moorehead |
| 6,527,754 B1 * | 3/2003 | Tallarida ............ A61M 39/0208 604/288.02 |
| 6,655,240 B1 | 12/2003 | DeVecchis et al. |
| 6,699,331 B1 | 3/2004 | Kritzler |
| 6,962,577 B2 * | 11/2005 | Tallarida ............ A61M 39/0208 604/288.02 |
| 6,981,977 B2 | 1/2006 | Herweck et al. |
| 7,056,316 B1 * | 6/2006 | Burbank ............. A61M 39/0208 604/288.01 |
| 7,131,962 B1 | 11/2006 | Estabrook et al. |
| 7,172,574 B2 | 2/2007 | Lundgren et al. |
| 7,272,997 B1 | 9/2007 | Lee et al. |
| 7,351,233 B2 | 4/2008 | Parks |
| 7,452,354 B2 | 11/2008 | Bright et al. |
| 7,618,462 B2 | 11/2009 | Ek |
| 7,713,251 B2 | 5/2010 | Tallarida et al. |
| 7,727,235 B2 | 6/2010 | Contiliano et al. |
| 7,803,143 B2 | 9/2010 | Tallarida et al. |
| 7,811,266 B2 | 10/2010 | Eliasen |
| 7,824,365 B2 | 11/2010 | Haarala et al. |
| 7,959,615 B2 | 6/2011 | Stats et al. |
| 8,182,453 B2 | 5/2012 | Eliasen |
| 8,409,153 B2 | 4/2013 | Tallarida et al. |
| 8,529,525 B2 | 9/2013 | Gerber et al. |
| 8,641,676 B2 * | 2/2014 | Butts ................. A61M 39/0247 604/164.01 |
| 8,656,929 B2 | 2/2014 | Miller et al. |
| 8,721,620 B2 | 5/2014 | Imran |
| 9,060,809 B2 | 6/2015 | Tipirneni et al. |
| 9,295,773 B2 * | 3/2016 | Prosl ................. A61M 1/3653 |
| 9,480,831 B2 | 11/2016 | Tallarida et al. |
| 9,597,783 B2 | 3/2017 | Zhang |
| 10,238,851 B2 | 3/2019 | Butziger et al. |
| 10,300,262 B2 | 5/2019 | Tallarida et al. |
| 10,369,345 B2 | 8/2019 | Tallarida et al. |
| 2001/0016713 A1 | 8/2001 | Takagi et al. |
| 2001/0037094 A1 * | 11/2001 | Adaniya ............ A61M 39/0208 604/288.01 |

(56) References Cited

U.S. PATENT DOCUMENTS

| | | |
|---|---|---|
| 2002/0095122 A1 | 7/2002 | Shaffer |
| 2002/0198527 A1 | 12/2002 | Muckter |
| 2003/0109837 A1 | 6/2003 | McBride-Sakal |
| 2004/0092875 A1 | 5/2004 | Kochamba |
| 2004/0097830 A1 | 5/2004 | Cooke et al. |
| 2004/0097930 A1 | 5/2004 | Justis et al. |
| 2004/0097941 A1 | 5/2004 | Weiner et al. |
| 2004/0147929 A1 | 7/2004 | Biedermann et al. |
| 2004/0158207 A1 | 8/2004 | Hunn et al. |
| 2005/0014993 A1 | 1/2005 | Mische |
| 2005/0085778 A1 | 4/2005 | Parks |
| 2005/0124980 A1* | 6/2005 | Sanders ............ A61M 39/0208 604/891.1 |
| 2005/0143735 A1 | 6/2005 | Kyle |
| 2005/0154373 A1 | 7/2005 | Deutsch |
| 2005/0165431 A1 | 7/2005 | Krivoruchko |
| 2005/0171493 A1 | 8/2005 | Nicholls |
| 2005/0209619 A1 | 9/2005 | Johnson et al. |
| 2005/0267421 A1 | 12/2005 | Wing |
| 2006/0004325 A1 | 1/2006 | Hamatake et al. |
| 2006/0142705 A1* | 6/2006 | Halili ................ A61M 5/14276 604/288.01 |
| 2006/0178648 A1 | 8/2006 | Barron et al. |
| 2006/0224129 A1* | 10/2006 | Beasley ............ A61M 39/0208 604/288.01 |
| 2006/0264988 A1 | 11/2006 | Boyle |
| 2007/0078432 A1 | 4/2007 | Halseth et al. |
| 2007/0100302 A1 | 5/2007 | Dicarlo et al. |
| 2007/0233019 A1 | 10/2007 | Forsell |
| 2007/0265595 A1 | 11/2007 | Miyamoto et al. |
| 2008/0039820 A1 | 2/2008 | Sommers et al. |
| 2008/0243106 A1 | 10/2008 | Coe et al. |
| 2008/0262475 A1 | 10/2008 | Preinitz |
| 2011/0137288 A1* | 6/2011 | Tallarida ............ A61M 39/0208 604/513 |
| 2011/0152901 A1 | 6/2011 | Woodruff et al. |
| 2011/0160699 A1 | 6/2011 | Imran |
| 2011/0264058 A1* | 10/2011 | Linden ............... A61M 39/0208 604/288.01 |
| 2011/0282285 A1* | 11/2011 | Blanchard ......... A61M 25/0097 604/164.08 |
| 2011/0301652 A1 | 12/2011 | Reed et al. |
| 2011/0311602 A1* | 12/2011 | Mills ....................... A01N 37/00 424/409 |
| 2012/0035585 A1* | 2/2012 | Kurrus ............... A61M 25/0668 604/508 |
| 2012/0053514 A1 | 3/2012 | Robinson et al. |
| 2012/0209180 A1 | 8/2012 | Gray et al. |
| 2012/0232501 A1 | 9/2012 | Eliasen |
| 2013/0081728 A1 | 4/2013 | Alsaffar |
| 2013/0116666 A1 | 5/2013 | Shih et al. |
| 2013/0218103 A1 | 8/2013 | Tallarida et al. |
| 2013/0226101 A1 | 8/2013 | Westcott |
| 2013/0231637 A1 | 9/2013 | Tallarida et al. |
| 2013/0274814 A1 | 10/2013 | Weiner et al. |
| 2014/0102445 A1* | 4/2014 | Clement ................ A61M 25/00 128/202.13 |
| 2014/0188179 A1 | 7/2014 | McCormick |
| 2014/0257165 A1 | 9/2014 | Shechtman et al. |
| 2014/0277191 A1 | 9/2014 | Evans et al. |
| 2015/0051584 A1* | 2/2015 | Korkuch ............ A61M 25/0606 604/510 |
| 2015/0273201 A1 | 10/2015 | Tallarida et al. |
| 2016/0175560 A1 | 6/2016 | Tallarida et al. |
| 2016/0175575 A1 | 6/2016 | Tallarida et al. |
| 2017/0000995 A1 | 1/2017 | Tallarida et al. |
| 2017/0014611 A1 | 1/2017 | Butziger et al. |
| 2017/0173273 A1 | 6/2017 | Tallarida et al. |
| 2017/0340814 A1 | 11/2017 | Miesel et al. |
| 2018/0104465 A1 | 4/2018 | Tallarida et al. |
| 2019/0192769 A1 | 6/2019 | Tallarida et al. |
| 2019/0351209 A1 | 11/2019 | Butziger et al. |

FOREIGN PATENT DOCUMENTS

| | | |
|---|---|---|
| EP | 3322460 | 5/2018 |
| EP | 3233175 | 3/2019 |
| GB | 2502291 | 11/2013 |
| JP | 55-065009 | 5/1980 |
| JP | 5506591 | 9/1993 |
| JP | 8500031 | 1/1996 |
| JP | 9-509852 | 10/1997 |
| JP | 2002119462 | 4/2002 |
| JP | 2002523131 | 7/2002 |
| JP | 2004167005 | 6/2004 |
| JP | 2004535234 | 11/2004 |
| JP | 2005522280 | 7/2005 |
| JP | 2008100084 | 5/2008 |
| JP | 2009-273598 | 11/2009 |
| JP | 2011120737 | 6/2011 |
| WO | 9701370 | 1/1997 |
| WO | 00/78231 | 12/2000 |
| WO | 0078231 | 12/2000 |
| WO | 2005025665 | 3/2005 |
| WO | 2005/094702 | 10/2005 |
| WO | 2007051563 | 5/2007 |
| WO | 2008126966 | 10/2008 |
| WO | 2009/148587 | 12/2009 |
| WO | 2015153976 | 10/2015 |
| WO | 2016/100868 | 6/2016 |
| WO | 2016/100945 | 6/2016 |
| WO | 2019126306 A1 | 6/2019 |

OTHER PUBLICATIONS

PCT Written Opinion dated Dec. 19, 2002 issued in PCT Application PCT/US01/13749, 5 pages.

PCT Preliminary Examination Report dated May 28, 2003 issued in PCT Application PCT/US01/13749, 2 pages.

European Examination Report dated Jul. 30, 2003 issued in European Patent Application No. 99 964 086.5, 5 pages.

U.S. Office Action dated Aug. 27, 2003 issued in U.S. Appl. No. 09/842,458, 8 pages.

U.S. Office Action dated Dec. 23, 2003 issued in U.S. Appl. No. 09/842,458, 7 pages.

European Examination Report dated Mar. 9, 2004 issued in European Patent Application No. 99 964 086.5, 4 pages.

U.S. Notice of Allowance dated Oct. 15, 2004 issued in U.S. Appl. No. 09/842,458, 7 pages.

Australian Examination Report dated Jan. 21, 2005 issued in Australian Patent Application No. 2001257388, 2 pages.

U.S. Notice of Allowance dated Feb. 24, 2005 issued in U.S. Appl. No. 09/842,458, 6 pages.

European Examination Report dated Mar. 1, 2005 issued in European Patent Application No. 99 964 086.5, 4 pages.

European Examination Report dated Mar. 30, 2005 issued in European Patent Application No. 99 964 086.5, 3 pages.

European Decision to Refuse dated Dec. 15, 2005 issued in European Patent Application No. 99 964 086.5, 9 pages.

U.S. Office Action dated Feb. 14, 2007 issued in U.S. Appl. No. 10/890,909, 12 pages.

U.S. Office Action dated Apr. 11, 2007 issued in U.S. Appl. No. 10/931,890, 7 pages.

U.S. Office Action dated Sep. 13, 2007 issued in U.S. Appl. No. 10/890,909, 11 pages.

U.S. Office Action dated Sep. 13, 2007 issued in U.S. Appl. No. 10/931,890, 7 pages.

Canadian Office Action dated Oct. 16, 2007 issued in Canadian Patent Application No. 2,407,643, 2 pages.

U.S. Office Action dated Feb. 21, 2008 issued in U.S. Appl. No. 11/269,098, 19 pages.

U.S. Office Action dated Jun. 9, 2008 issued in U.S. Appl. No. 10/931,890, 10 pages.

U.S. Office Action dated Oct. 30, 2008 issued in U.S. Appl. No. 11/269,098, 12 pages.

U.S. Office Action dated Dec. 23, 2008 issued in U.S. Appl. No. 10/931,890, 9 pages.

(56) References Cited

OTHER PUBLICATIONS

U.S. Office Action dated Jun. 4, 2009 issued in U.S. Appl. No. 11/269,098, 11 pages.
Supplemental European Search Report dated Jun. 10, 2009 issued in European Patent Application No. 01 930 898.0, 4 pages.
U.S. Office Action dated Aug. 3, 2009 issued in U.S. Appl. No. 10/931,890, 10 pages.
European Examination Report dated Oct. 2, 2009 issued in European Patent Application No. 01 930 898.0, 4 pages.
U.S. Office Action dated Mar. 3, 2010 issued in U.S. Appl. No. 11/269,098, 15 pages.
U.S. Office Action dated Feb. 17, 2011 issued in U.S. Appl. No. 12/902,839, 17 pages.
U.S. Office Action dated Oct. 17, 2011 issued in U.S. Appl. No. 12/902,839, 11 pages.
Notice of Allowance dated Feb. 1, 2012 issued in U.S. Appl. No. 12/902,839, 7 pages.
European Office Action dated Oct. 23, 2012 issued in European Patent Application No. 01 930 898.0, 4 pages.
U.S. Office Action dated Feb. 28, 2007 issued in U.S. Appl. No. 10/374,000, 8 pages.
U.S. Office Action dated Aug. 28, 2007 issued in U.S. Appl. No. 10/374,000, 8 pages.
U.S. Office Action dated Mar. 20, 2008 issued in U.S. Appl. No. 10/374,000, 7 pages.
U.S. Office Action dated Sep. 30, 2008 issued in U.S. Appl. No. 10/374,000, 8 pages.
U.S. Office Action dated May 20, 2009 issued in U.S. Appl. No. 10/374,000, 10 pages.
Access technologies, The V-A-Pu . . . Vascular Access and Beyond, downloaded from internet Jul. 28, 2009, http://www.norfolkaccess.com/VAPs.html, 4 pages.
SyncMedical, Innovative Surgical Devices, Primo Port Products, downloaded from internet Jul. 28, 2009, http://www.syncmedical.com/primo-port, 2 pages.
Corrected Notice of Allowability dated Jul. 12, 2016, issued in U.S. Appl. No. 13/770,732, 6 pages.
Corrected Notice of Allowability dated Aug. 2, 2016, issued in U.S. Appl. No. 13/770,732, 6 pages.
International Search Report and Written Opinion dated Oct. 7, 2016, issued in PCT International Patent Application No. PCT/US2016/042272, 11 pages.
International Preliminary Report on Patentability dated Oct. 13, 2016, issued in PCT International Patent Application No. PCT/US2015/023590, 9 pages.
International Preliminary Report on Patentability dated Oct. 13, 2016, issued in PCT International Patent Application No. PCT/US2015/024256, 8 pages.
U.S. Office Action dated Oct. 23, 2014 issued in U.S. Appl. No. 13/477,997, 14 pages.
European Extended Search Report dated Nov. 27, 2017, issued in European Patent Application No. 15772648.0, 7 pages.
Office Action dated Nov. 30, 2017, issued in U.S. Appl. No. 15/210,268, 15 pages.
Preliminary Report on Patentability dated Jan. 25, 2018, issued in PCT Patent Application No. PCT/US2016/042272, 9 pages.
U.S. Office Action dated Nov. 30, 2016, issued in U.S. Appl. No. 14/231,392, 6 pages.
Office Action dated Aug. 31, 2017, issued in U.S. Appl. No. 14/974,851, 12 pages.
Search Report dated Nov. 8, 2017, issued in European Patent Application No. 15773029.2, 8 pages.
U.S. Office Action dated Dec. 2, 2014, issued in U.S. Appl. No. 13/770,732, 15 pages.
U.S. Office Action dated Jun. 10, 2015, issued in U.S. Appl. No. 13/770,732, 14 pages.
International Search Report and Written Opinion dated Jul. 2, 2015, issued in PCT Patent Application No. PCT/US2015/023590, 11 pages.
International Search Report and Written Opinion dated Jul. 10, 2015, issued in PCT Patent Application No. PCT/US2015/024256, 10 pages.
U.S. Office Action dated Aug. 10, 2015, issued in U.S. Appl. No. 14/231,392, 24 pages.
U.S. Office Action dated Jan. 15, 2016, issued in U.S. Appl. No. 13/770,732, 23 pages.
International Search Report and Written Opinion dated Feb. 26, 2016, issued in PCT Patent Application Serial No. PCT/US2015/066934, 11 pages.
International Search Report and Written Opinion dated Mar. 7, 2016, issued in PCT Patent Application Serial No. PCT/US2015/066778, 9 pages.
Final Office Action dated Mar. 22, 2016, issued in U.S. Appl. No. 14/231,392, 22 pages.
Notice of Allowance dated Jun. 15, 2016, issued in U.S. Appl. No. 13/770,732, 9 pages.
Office Action dated Jun. 27, 2018, issued in U.S. Appl. No. 15/300,625, 14 pages.
Extended Search Report dated Jul. 4, 2018, issued in European Patent Application No. 15871254.7, 5 pages.
Partial Supplementary Search Report dated Aug. 2, 2018, issued in European Patent Application No. 15871198.6, 13 pages.
Office Action dated Aug. 29, 2018, issued in U.S. Appl. No. 15/267,537, 8 pages.
Notice of Allowance dated Sep. 12, 2018, issued in U.S. Appl. No. 15/210,268, 12 pages.
Intent to Grant dated Oct. 4, 2018, issued in European Patent Application No. 15871254.7, 7 pages.
Office Action dated Feb. 26, 2018, issued in U.S. Appl. No. 14/974,851, 12 pages.
Notice of Allowance dated Mar. 18, 2019, issued in U.S. Appl. No. 15/300,625, 8 pages.
Office Action dated Jun. 13, 2019, issued in U.S. Appl. No. 14/974,851, 11 pages.
Extended Search Report dated Dec. 12, 2018, issued in European Patent Application No. 15871198.6, 15 pages.
Examination Report dated Jan. 16, 2019, issued in Australian Patent Application No. 2015240568, 5 pages.
Decision to Grant dated Feb. 5, 2019, issued in Japanese Patent Application No. 2017-503777, 4 pages.
Office Action dated Feb. 6, 2019, issued in U.S. Appl. No. 15/301,498, 10 pages.
Extended Search Report dated Mar. 1, 2019, issued in European Patent Application No. 16825172.6, 7 pages.
Office Action dated Oct. 17, 2018, issued in U.S. Appl. No. 15/301,498, 14 pages.
Notice of Allowance dated Oct. 30, 2018, issued in U.S. Appl. No. 15/210,268, 11 pages.
Office Action dated Jan. 7, 2019, issued in U.S. Appl. No. 14/974,851, 12 pages.
Notice of Allowance dated Jan. 10, 2019, issued in U.S. Appl. No. 15/267,537, 8 pages.
International Search Report and Written Opinion dated Mar. 21, 2019, issued in PCT International Patent Application No. PCT/US2018/066472, 9 pages.
Office Action dated Nov. 30, 2018, issued in European Patent Application No. 15 772 648.0, 4 pages.
Office Action dated Dec. 25, 2018, issued in Japanese Patent Application No. 2017-503790, 12 pages. English language machine translation provided.
Examination Report dated Jan. 10, 2019, issued in Australian Patent Application No. 2015240953, 5 pages.
Office Action dated Oct. 1, 2019, issued in Japanese Patent Application No. 2017-532627, 9 pages.
Office Action dated Oct. 1, 2019, issued in Japanese Patent Application No. 2017-532615, 5 pages.
Intent to Grant dated Dec. 10, 2019, issued in European Patent Application No. 15 773 029.2, 6 pages.
Notice of Allowance dated Jul. 3, 2019, issued in Australian Patent Application No. 2015240953, 4 pages.
Notice of Allowance dated Aug. 8, 2019, issued in Australian Patent Application No. 2015240568, 4 pages.

(56) References Cited

OTHER PUBLICATIONS

Examination Report dated Aug. 14, 2019, issued in Australian Patent Application No. 2015364276, 4 pages.
Examination Report dated Aug. 21, 2019, issued in Australian Patent Application No. 2015364382, 5 pages.
Notice of Allowance dated Aug. 27, 2019, issued in U.S. Appl. No. 15/301,498, 10 pages.
Office Action dated Nov. 26, 2019, issued in U.S. Appl. No. 15/835,858, 15 pages.
Decision to Grant dated Feb. 4, 2020, issued in Japanese Patent Application No. 2017-532615, 4 pages. English language summary provided.
Examination Report dated Mar. 23, 2020, issued in Australian Patent Application No. 2016294584, 6 pages.
Notice of Acceptance dated Apr. 20, 2020, issued in Australian Patent Application No. 2015364276, 4 pages.
Office Action dated Mar. 27, 2020, issued in U.S. Appl. No. 14/974,851, 12 pages.

\* cited by examiner

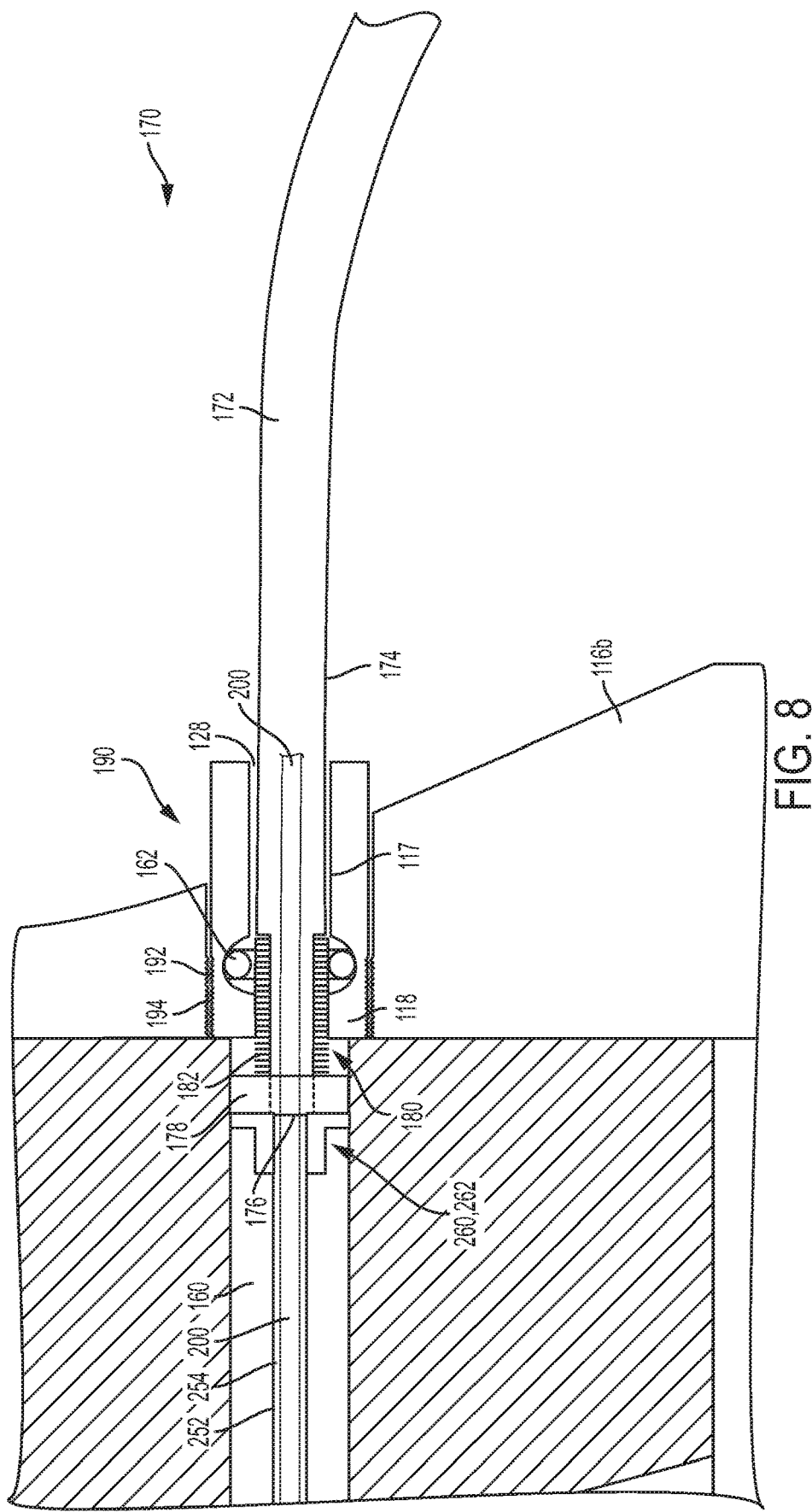

DEVICES, SYSTEMS AND METHODS FOR REMOVAL AND REPLACEMENT OF A CATHETER FOR AN IMPLANTED ACCESS PORT

CROSS-REFERENCE TO RELATED APPLICATIONS

The present application claims the benefit of the filing date of U.S. provisional patent application Ser. No. 62/093,769 filed Dec. 18, 2014, the entire disclosure of which is incorporated herein by reference.

FIELD

The present disclosure relates to medical devices, systems and methods, and more particularly to medical devices, systems and methods for removal and replacement of an implanted catheter connected to an implanted access port, particularly an implanted vascular access catheter connected to an implanted vascular access port.

BACKGROUND

Medical patients, such as oncology patients, hemodialysis patients and hematology patients, may be subject to frequent fluid infusion treatments (e.g. delivering fluids comprising pharmaceuticals, blood, nutrients, contrasting agents and other compositions) and/or fluid extraction treatments (e.g. removing fluid comprising blood as part of phlebotomy). Frequent "needle sticks" and the duration of infusion time may make receiving such treatments difficult and/or uncomfortable, and may create scarring and added discomfort to the patient.

Vascular access ports may now be inserted beneath the cutaneous tissue (skin) of the patient to reduce discomfort and increase efficiency associated with such treatments. A vascular access port may include an access point, such as a septum, into which a needle may be inserted, or a needle residing in the vascular access port may be raised from under and through the cutaneous tissue.

An implanted vascular access (indwelling) catheter is ordinarily connected to an implanted vascular access port. The vascular access catheter may be inserted into a vein, such as a jugular vein, subclavian vein or the superior vena cava.

Vascular access catheters are known to be connected to the vascular access port by providing the vascular access port with a male (stem) fitting including a plurality of conical barbs which are designed to engage within the lumen inside of the vascular access catheter. In light of such, once such a vascular access port and catheter are implanted, there is no non-surgical way to remove and replace the vascular access catheter without reopening the implantation (surgical) site.

Unfortunately, maintaining the patency of a vascular access catheter may become more difficult over time. In-growth and blood clotting may clog and inhibit fluid flow through the vascular access catheter, either by reducing fluid flow or completely preventing fluid flow. One method of trying to maintain patency may include flushing the vascular access catheter with saline or other fluid agents, but such approaches may have only limited success and suffer from several disadvantages. Once in-growth has begun, the efficacy of flushing alone may become limited. Moreover, material removed by the flushing may be deposited into the vasculature, and could be deposited elsewhere in the circulatory system.

SUMMARY

The present disclosure relates to medical devices, systems and methods, and more particularly to medical devices, systems and methods for removal and replacement of an implanted catheter connected to an implanted access port, particularly an implanted vascular catheter connected to an implanted vascular access port.

In certain embodiments, a medical device may comprise an implantable vascular access port including a fluid passage operable to introduce fluid to a host and/or remove fluid from the host, the fluid passage accessible through a fluid passage access opening and at least a portion of the fluid passage defined by a needle configured to penetrate cutaneous tissue of the host, and an implantable vascular access catheter connectable with the vascular access port, wherein the vascular access catheter and the vascular access port are connectable to each other within the vascular access port.

As set forth by the present disclosure, by establishing a connection between the vascular access catheter and the vascular access port within the vascular access port (as opposed to a vascular access catheter being connected to the vascular access port by providing the vascular access port with a male stem fitting), the vascular access catheter may be removed from the host and replaced without having to open a surgical sight.

In certain embodiments, the vascular access catheter is insertable into the fluid passage of the vascular access port through the fluid passage access opening and removable from the fluid passage of the vascular access port through the fluid passage access opening.

In certain embodiments, the portion of the fluid passage defined by the needle is defined by a lumen of the needle, and the vascular access catheter is insertable into the lumen of the needle through the fluid passage access opening and removable from the lumen of the needle through the fluid passage access opening.

In certain embodiments, the vascular access catheter and the vascular access port are connectable to each other within the vascular access port by a mechanical connection.

In certain embodiments, the mechanical connection comprises at least one of a friction fit connection and a positive mechanical engagement connection.

In certain embodiments, the positive mechanical engagement connection comprises an overlapping connection formed by a proximal end portion of the vascular access catheter and a portion of the vascular access port.

In certain embodiments, the overlapping connection is formed by a flange of the vascular access catheter overlapping with a shoulder of the vascular access port.

In certain embodiments, the friction fit connection comprises a press-fit connection formed by a proximal end portion of the vascular access catheter and a portion of the vascular access port.

In certain embodiments, the vascular access port includes a catheter egress opening, and the press-fit connection is formed by at least one resilient deformable retention element of the vascular access catheter deforming against a sidewall of the catheter egress opening when located in the catheter egress opening of the vascular access port.

In certain embodiments, the vascular access catheter comprises a tubular body and a proximal end portion which are insertable into the fluid passage of the vascular access port through the fluid passage access opening and, when the tubular body and the proximal end portion of the vascular access catheter are inserted into the fluid passage of the vascular access port, the tubular body of the vascular access catheter extends from a catheter egress opening of the vascular access port while a mechanical interference inhibits the proximal end portion of the vascular access catheter from passing through the vascular access port and being removed from the vascular access port through the catheter egress opening.

In certain embodiments, the fluid passage of the vascular access port has a fluid passage diameter and the catheter egress opening of the vascular access port has a catheter egress opening diameter, wherein the proximal end portion of the vascular access catheter has a diameter smaller than the fluid passage diameter and larger than the catheter egress opening diameter, and wherein the mechanical interference which inhibits the proximal end portion of the vascular access catheter from passing through the vascular access port and being removed from the vascular access port through the catheter egress opening is formed by the proximal end portion of the vascular access catheter have a diameter larger than the catheter egress opening diameter.

In certain embodiments, the vascular access port includes a housing, and the connection within the vascular access port is formed with the housing.

In certain embodiments, the housing includes a catheter egress opening, and the connection within the vascular access port is formed with a portion of the housing defining at least a portion of the catheter egress opening.

In certain embodiments, the housing includes a stem extending outward from a wall of the housing, and the catheter access opening is provided in the stem.

In certain embodiments, the housing includes a catheter retention member connected to a wall of the housing, and the catheter access opening is provided in the catheter retention member.

In certain embodiments, the catheter retention member is disconnectable from the wall of the housing, and comprises at least one screw thread which threadably engages with at least one screw thread of the housing.

In certain embodiments, the vascular access catheter is connectable with the vascular access port within the fluid passage of the vascular access port.

In certain embodiments, the present disclosure provides a catheter insertion tool configured to insert the vascular access catheter into the vascular access port through the fluid passage access opening and the fluid passage of the vascular access port.

In certain embodiments, the catheter insertion tool is further configured to engage a mechanical connection between the vascular access catheter and the vascular access port, and the catheter insertion tool is configured to operate with a guidewire.

In certain embodiments, the present disclosure provides a catheter removal tool configured to remove the vascular access catheter from the vascular access port through the fluid passage and the fluid passage access opening of the vascular access port.

In certain embodiments, the catheter removal tool is further configured to disengage a mechanical connection between the vascular access catheter and the vascular access port, and the catheter removal tool is configured to operate with a guidewire.

In certain embodiments, the catheter removal tool comprises a distal end tip configured to mechanically connect with a proximal end portion of the vascular access catheter.

In certain embodiments, a method of operating a medical device may comprise operating an implanted vascular access port and a first vascular access catheter connected to the vascular access port and extending into a blood vessel of a host such that a needle of the vascular access port penetrates through cutaneous tissue of the host to become exposed above the cutaneous tissue; establishing access to a fluid passage of the vascular access port through a fluid passage access opening of the needle, the fluid passage operable to introduce fluid to the host and/or remove fluid from the host; introducing a guidewire into the fluid passage of the vascular access port, through a lumen of the first vascular access catheter and into a lumen of a blood vessel of the host; positioning a catheter removal tool on the guidewire; introducing the catheter removal tool into the fluid passage of the vascular access port; engaging the catheter removal tool with the first vascular access catheter; removing the first vascular access catheter from the host through the fluid passage of the vascular access port with the catheter removal tool; removing the catheter removal tool and the first vascular access catheter from the guidewire; positioning a second vascular access catheter on the guidewire; positioning a catheter insertion tool on the guidewire; introducing the second vascular access catheter and the catheter insertion tool into the fluid passage of the vascular access port; introducing the second vascular access catheter into the host such that the second vascular access catheter extends from the vascular access port to the lumen of the blood vessel of the host; removing the catheter insertion tool from the fluid passage of the vascular access port; and removing the guidewire from the lumen of the blood vessel of the host, through a lumen of the second vascular access catheter and from the fluid passage of the vascular access port.

In certain embodiments, a method of operating a medical device may comprise disengaging a mechanical connection between the first vascular access catheter and the vascular access port after engaging the first vascular access catheter with the catheter removal tool.

In certain embodiments, a method of operating a medical device may comprise engaging a mechanical connection between the second vascular access catheter and the vascular access port after introducing the second vascular access catheter into the host.

FIGURES

Features and advantages of the claimed subject matter will be apparent from the following detailed description of some example embodiments consistent therewith, which description should be considered with reference to the accompanying drawings, wherein:

Figure 1:
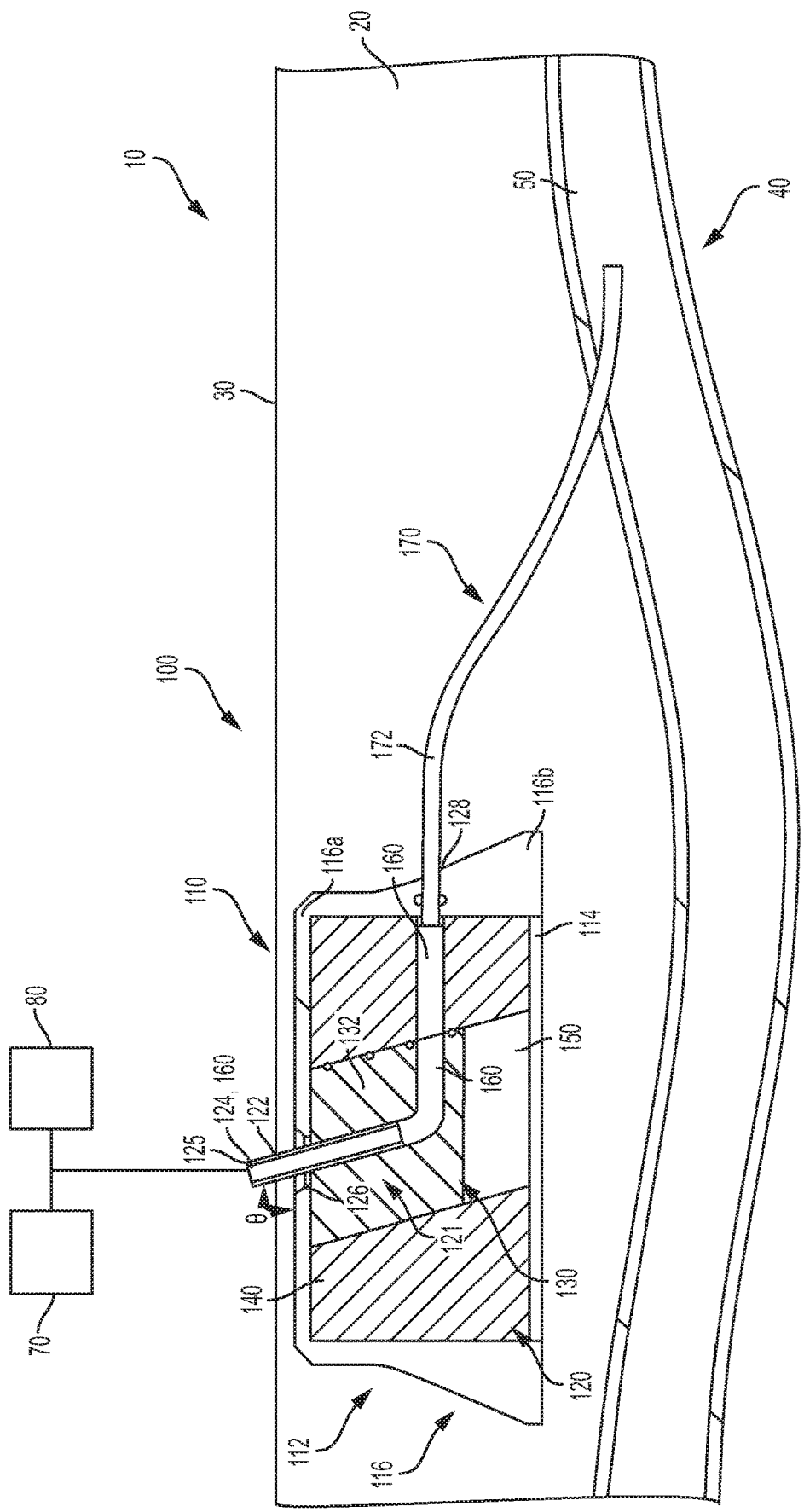
FIG. 1 illustrates a cross-sectional view of a vascular access port and a vascular access catheter implanted in a host, particularly beneath cutaneous (skin) tissue with a needle of the vascular access port extended and penetrating through the cutaneous tissue of the host to become exposed above the cutaneous tissue.
Figure 4:
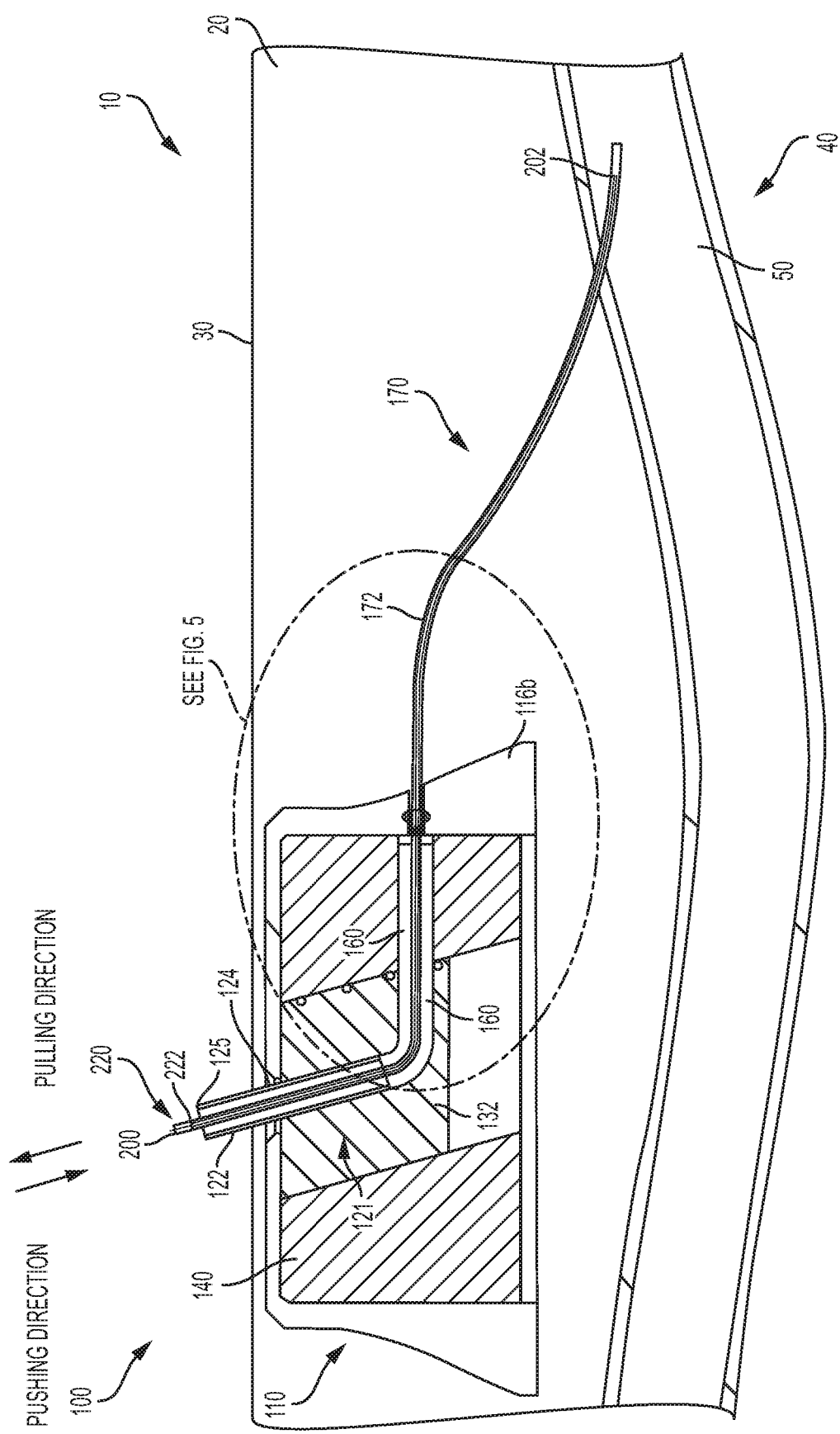
Figure 5:
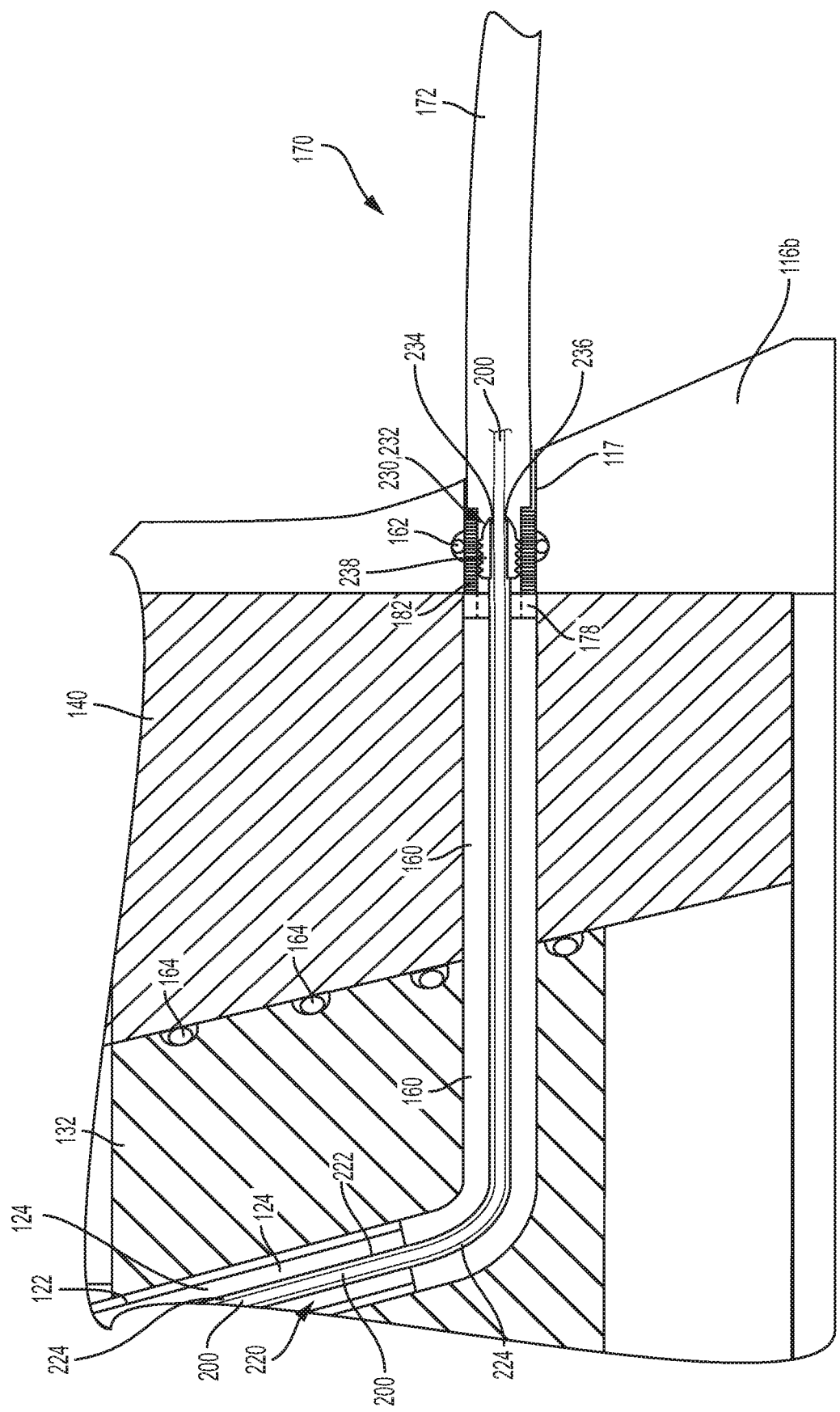
Figure 6:
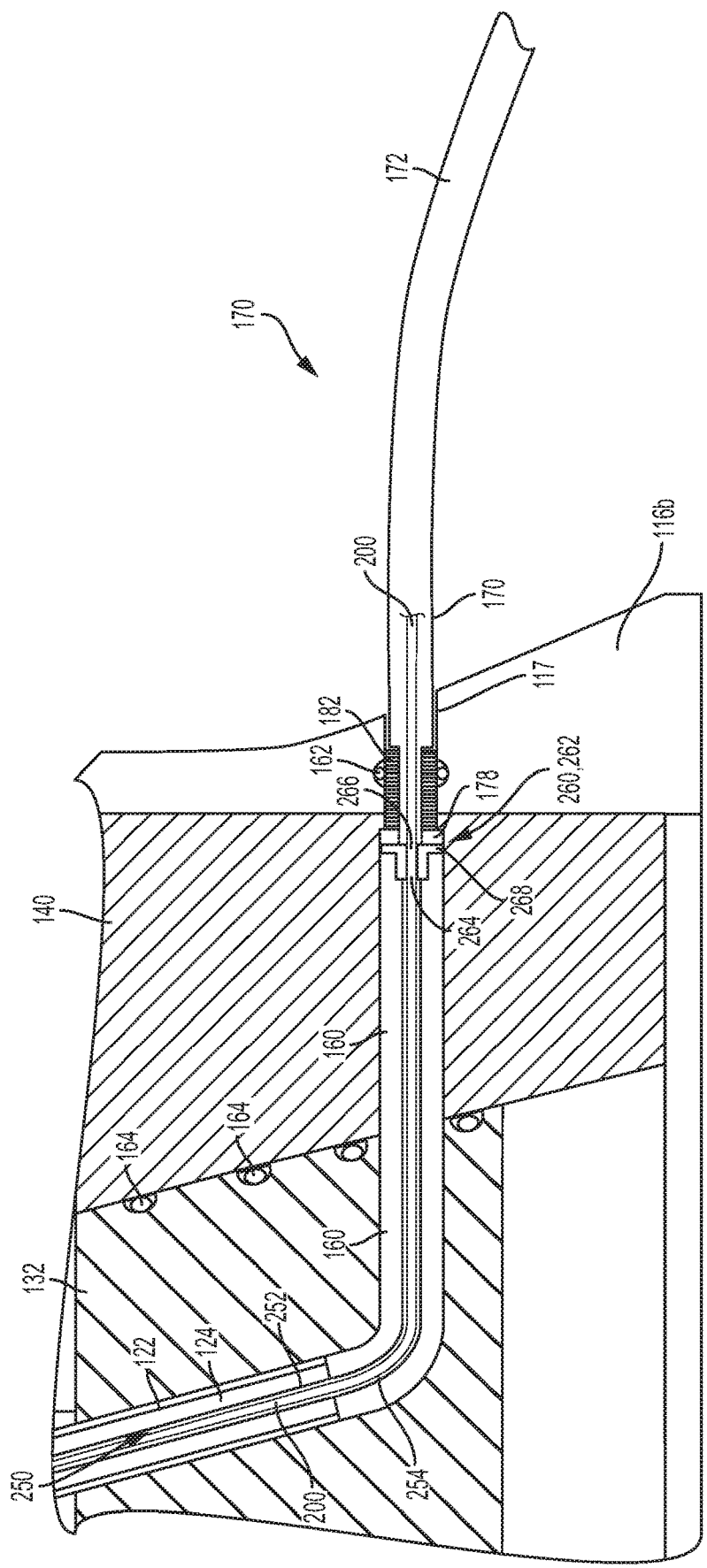
Figure 7:
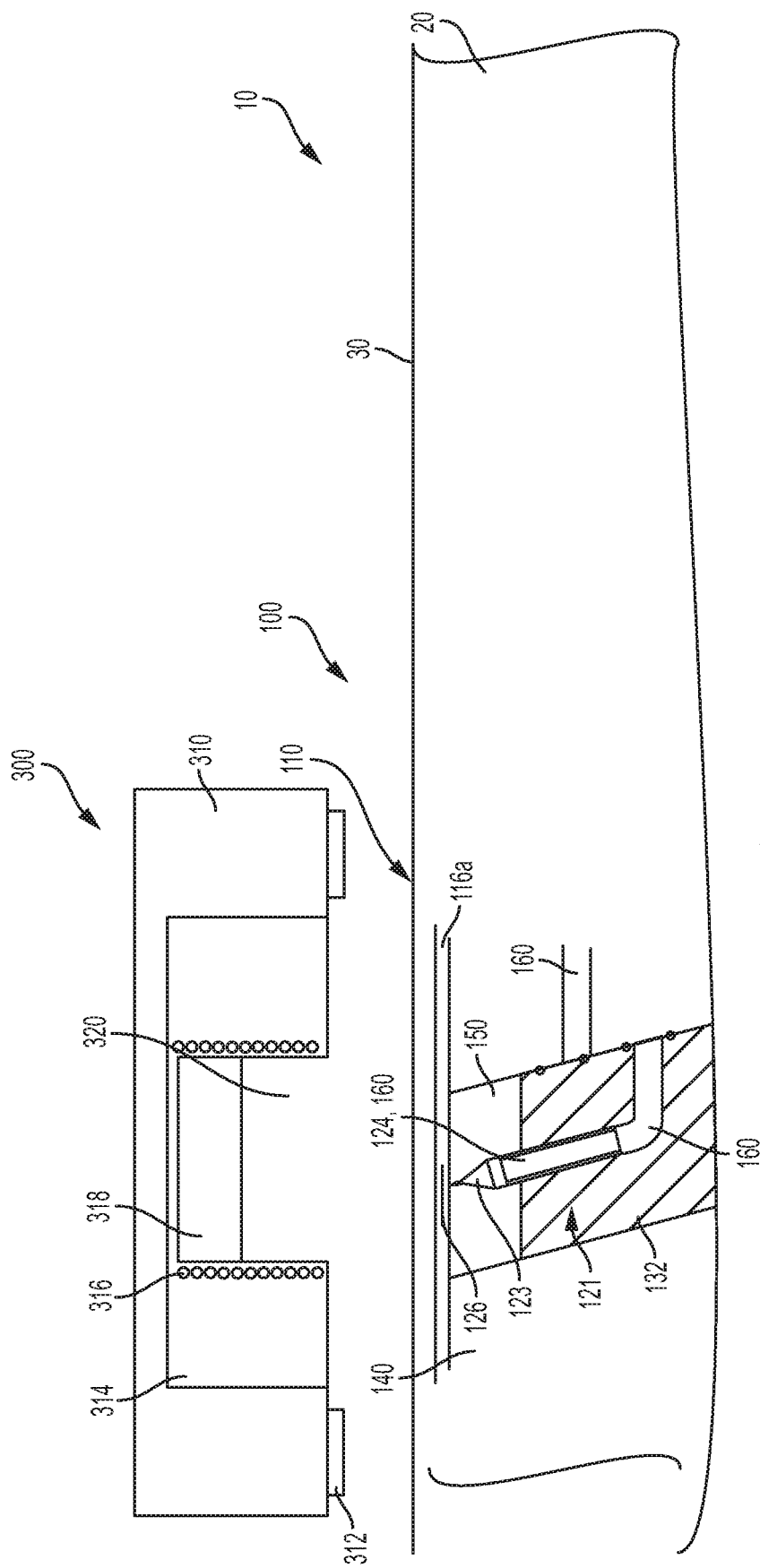

FIG. 4 is a cross-sectional view of the vascular access port and the vascular access catheter of FIG. 1, with a guidewire inserted in the vascular access port and the vascular access catheter, and a catheter removal tool inserted in the vascular access port; and FIG. 5 is a close-up cross-sectional view of the distal end of the catheter removal tool and a guidewire inserted in the lumen of the vascular access catheter of FIG. 4;

FIG. 6 is a close-up cross-sectional view of the distal end of a catheter insertion tool and a replacement vascular access catheter arranged on the guidewire in the vascular access port of FIG. 1;

FIG. 7 illustrates a cross-sectional view of the vascular access port and the vascular access catheter of FIG. 1 implanted in a host, particularly beneath cutaneous (skin) tissue with the needle of the vascular access port retracted into the vascular access port; and FIG. 8 is a close-up cross-sectional view of the connection formed between the vascular access port and the vascular access catheter according to another embodiment of the disclosure.

DETAILED DESCRIPTION

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

By way of a general overview, the present disclosure provides medical devices, systems and methods for removal and replacement of an implanted access catheter connected to an implanted access port. According to at least one embodiment of the disclosure, a medical device may be provided which comprises an implantable vascular access port including a fluid passage operable to introduce fluid to a host and/or remove fluid from the host, the fluid passage accessible through a fluid passage access opening and at least a portion of the fluid passage defined by a needle configured to penetrate cutaneous tissue of the host, and an implantable vascular access catheter connectable with the vascular access port, wherein the vascular access catheter and the vascular access port are connectable to each other within the vascular access port.

As disclosed herein, mechanical connections formed between the components herein may include friction fit connections (which may also be referred to an interference or press fit) and positive mechanical engagement connections. A friction fit connection may be understood as a connection formed between the components which solely relies upon friction to inhibit separation of the components, particularly by one of the components being pressed into the other component such that at least one of the components is compressed (deformed) against the another. On the other hand, a positive mechanical engagement connection may be understood as a connection formed between the components which does not rely solely on friction to inhibit separation of the components and which includes a mechanical interlock to inhibit separation of the components (e.g. overlapping surfaces).

Referring now to the figures, and particularly to FIG. 1, there is shown a medical device 100 according to the present disclosure. Medical device 100 may comprise an implantable (sub-cutaneous) vascular access port 110. As shown, vascular access port 110 is implanted in a host 10 (e.g. patient, which may be undergoing medical treatment or diagnosis), particularly beneath the surface 30 of cutaneous (skin) tissue 20.

As shown, vascular access port 110 may comprise an outer housing 112 including a base 114 supporting a cover 116, which may be made of a suitable (biocompatible) thermoplastic polymer composition, or metal such as titanium. Housing 112 may include an internal needle elevator mechanism 120 which may extend a pointed, closed tip, hollow needle 121 (for better clarity, a pointed, removable, atraumatic, dilator tip 123 as shown in FIG. 7 has been removed from shaft 122) out from the housing 112 or retract the needle 121 into the housing 112 through an opening 126 formed in the housing 112 (which may be provided in a self-sealing septum or other self-closing membrane which provides a seal) on the top wall 116a of the housing 112 closest to the surface 30 of cutaneous (skin) tissue 20.

As shown, needle elevator mechanism 120 comprises a movable needle platform 130 which comprises a piston 132 to extend the needle 121 out of the housing 112 and to retract the needle 121 into the housing 112. The piston 132 of the needle platform 130 may move the needle 121 relative to a surrounding support structure 140 which defines a chamber 150 in which the needle platform 130 travels in opposing directions to extend and retract the needle 121. As shown, the needle elevator mechanism 120, and more particularly piston 132, may be configured to extend the needle 121 out of the housing 112 and to retract the needle 121 into the housing 112 at an extension/retraction angle θ, relative to the top wall 116a of the housing 112 (and/or the surface 30 of cutaneous (skin) tissue 20) in a range between 10 degrees and 90 degrees. More particularly, the extension/retraction angle θ may be in a range of 45 degrees to 90 degrees.

Vascular access port 110 further includes an elongated L-shaped fluid flow passage 160, which may be formed at least in part by a tubular (cylindrical) bore which extends through piston 132 of needle platform 130, and through the needle platform support structure 140. The fluid flow passage 160 is operable to introduce fluid to the host 10 from a fluid source 70 and/or remove fluid from the host 10 to a fluid receptacle 80.

The fluid flow passage 160 is accessible through fluid passage access opening 125. Fluid passage access opening 125 may be covered with a pointed, removable tip (shown at 123 in FIG. 7), which is at the end of the shaft 122 of needle 121, to keep the needle lumen 124 closed to ingress of fluid(s) (particularly body fluid(s)), as well as to allow for limited-volume flushing, when the vascular access port 110 is not in use, particularly when the needle 121 is retracted. As shown, at least a portion of the fluid flow passage 160 is defined by the lumen 124 of the needle 121, which may be particularly configured to penetrate the cutaneous tissue 20 of host 10. The needle 121 may be press-fit into the bore formed in the piston 132 other otherwise secured (e.g. mechanically or adhesively) within the bore.

Medical device 100 further comprises an implantable (indwelling) vascular access catheter 170 which is connectable with the vascular access port 110. The vascular access catheter 170 may particularly extend from the vascular access port 110 into a lumen 50 of a blood vessel 40 in the tissue 20 of the host 10. As shown by FIG. 1, the vascular access catheter 170 and the vascular access port 110 are connectable to each other within the vascular access port 110. The vascular access catheter 170 may be made of a suitable (biocompatible) thermoplastic polymer composition, such as a thermoplastic elastomer, or other suitable material.

As described in greater detail below, the vascular access catheter 170 is insertable into the fluid flow passage 160 of the vascular access port 110 through the fluid passage access opening 125 and removable from the fluid flow passage 160 of the vascular access port 110 through the fluid passage access opening 125. Furthermore, for the portion of the fluid flow passage 160 defined by the needle 121, as more particularly defined by the lumen 124 of the needle 121, it should be understood that the vascular access catheter 170 is insertable into the lumen 124 of the needle 121 through the fluid passage access opening 125 and removable from the lumen 124 of the needle 121 through the fluid passage access opening 125.

Figure 2:
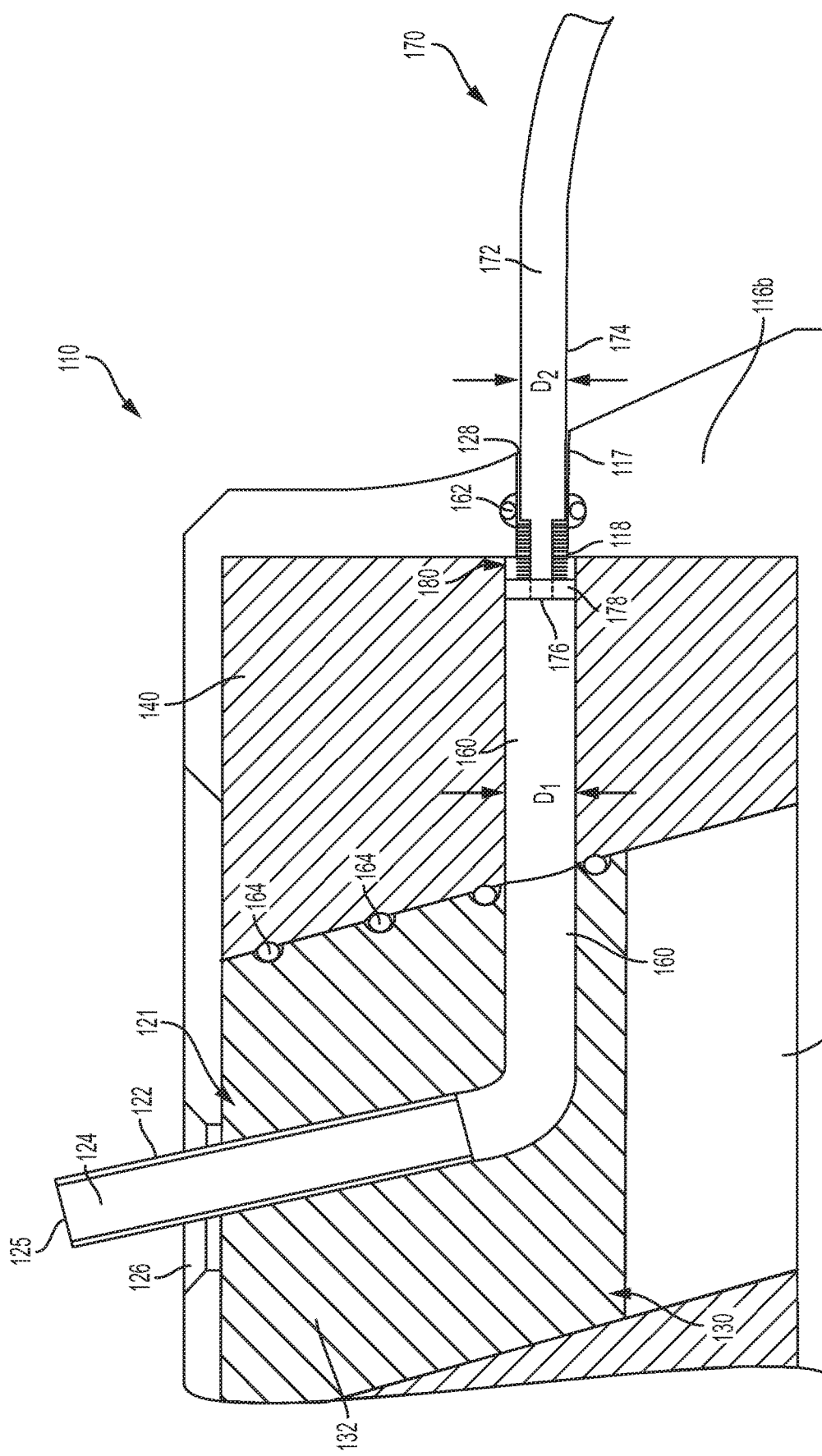
FIG. 2 is a close-up cross-sectional view of a section of the vascular access port and a section the vascular access catheter of FIG. 1 at the connection thereof.

Referring now to FIG. 2, there is shown a close-up view of a section of the vascular access port 110 and a section of the vascular access catheter 170. As mentioned above, and further explained below, the vascular access catheter 170 is particularly configured to be insertable and removable from the host 10 through the vascular access port 110. In the foregoing manner, should the vascular access catheter 170 become partially or fully occluded, it is possible to remove the vascular access catheter 170 without open surgery of the host 10 to remove the first (occluded) vascular access catheter 170 and replace the vascular access catheter 170 with a second (unoccluded) vascular access catheter 170.

As shown by FIG. 2, the fluid flow passage 160 leads distally to a catheter egress opening 128 formed in the cover 116 of the housing 112. As explained in greater detail below, in order to form a mechanical connection between the vascular access catheter 170 and the vascular access port 110 within the vascular access port 110, the catheter egress opening 128 may have a smaller diameter $D_2$ than the diameter $D_1$ of the fluid flow passage 160, which results in a circular annular shoulder 118 at the decrease in diameter.

As shown, the flexible tubular body 174 of the vascular access catheter 170, shown as a cylindrical sidewall, has a diameter which is slightly less than the smaller diameter $D_2$ of the catheter egress opening 128 (as compared to the diameter $D_1$ of the fluid flow passage 160). As a result, the tubular body 174 of the vascular access catheter 170 may extend (pass) through the fluid flow passage 160 and the catheter egress opening 128.

However, while the tubular body 174 of the vascular access catheter 170 may freely extend (pass) through the catheter egress opening 128, a proximal end portion 180 of the vascular access catheter 170 will not extend (pass) through catheter egress opening 128. More particularly, the proximal terminal end 176 of the vascular access catheter 170 includes a circular annular flange 178 which has a diameter which is greater than diameter $D_2$ of catheter egress opening 128 (and slightly less than diameter $D_1$ of the of the fluid flow passage 160). It should be understood that the term "proximal", as well as the term "distal" with regards to the vascular access catheter 170 is used in reference to the vascular access port 110 and, as such the distal terminal end of the vascular access catheter 170 should be understood to be inserted into the lumen 50 of the blood vessel 40 of the host 10.

As such, as the tubular body 174 is inserted into fluid flow passage 160 through fluid passage access opening 125, the vascular access catheter 170 may freely extend (pass) through the fluid flow passage 160 and catheter egress opening 128 of the vascular access port 110 until the flange 178 of the vascular access catheter 170 makes contact with shoulder 118 of the vascular access port 110, provided by sidewall 116b of cover 116 of housing 112, which will prevent the vascular access catheter 170 from being removed from the vascular access port 110 through sidewall 116b of cover 116 by virtue of the overlap created between the flange 178 of the vascular access catheter 170 and the shoulder 118 of the vascular access port 110 provided by sidewall 116b of cover 116. The overlap created between the flange 178 of the vascular access catheter 170 and the shoulder 118 of the vascular access port 110 provides a mechanical (overlapping) connection, which may also be referred to as a mechanical interference, within the inside of the vascular access port 110 between the vascular access catheter 170 and the vascular access port 110. As shown, the connection is formed with a portion of the vascular access port 110, here shoulder 118 provided by housing 112, which defines at least a portion of the catheter egress opening 128. More particularly, the overlap created provides a positive mechanical engagement connection between the vascular access catheter 170 and the vascular access port 110.

Even more particularly, the overlap created provides a one-way positive mechanical engagement connection between the vascular access catheter 170 and the vascular access port 110. In other words, while the positive mechanical engagement prevents the vascular access catheter 170 from being pulled from the vascular access port 110 through the catheter egress opening 128 of the vascular access port 110, the positive mechanical engagement does not prevent the vascular access catheter 170 from being pulled from the vascular access port 110 through the fluid passage access opening 125 to replace the vascular access catheter 170.

To prevent body fluids (e.g. blood) of the host 10 which surround the vascular access catheter 170 from ingress into the vascular access port 110, the vascular access port 110 may include a seal member 162 (e.g. O-ring) which seals against the tubular body 174 of the vascular access catheter 170. Furthermore, vascular access port 110 may also include one of more seal members 164 (e.g. O-rings) to prevent body fluids of the host 10 located in the fluid flow passage 160 of the vascular access port 110 from ingress between needle platform 130 and the surrounding support structure 140, as well as chamber 150, particularly when the piston 132 is not activated.

Figure 3:
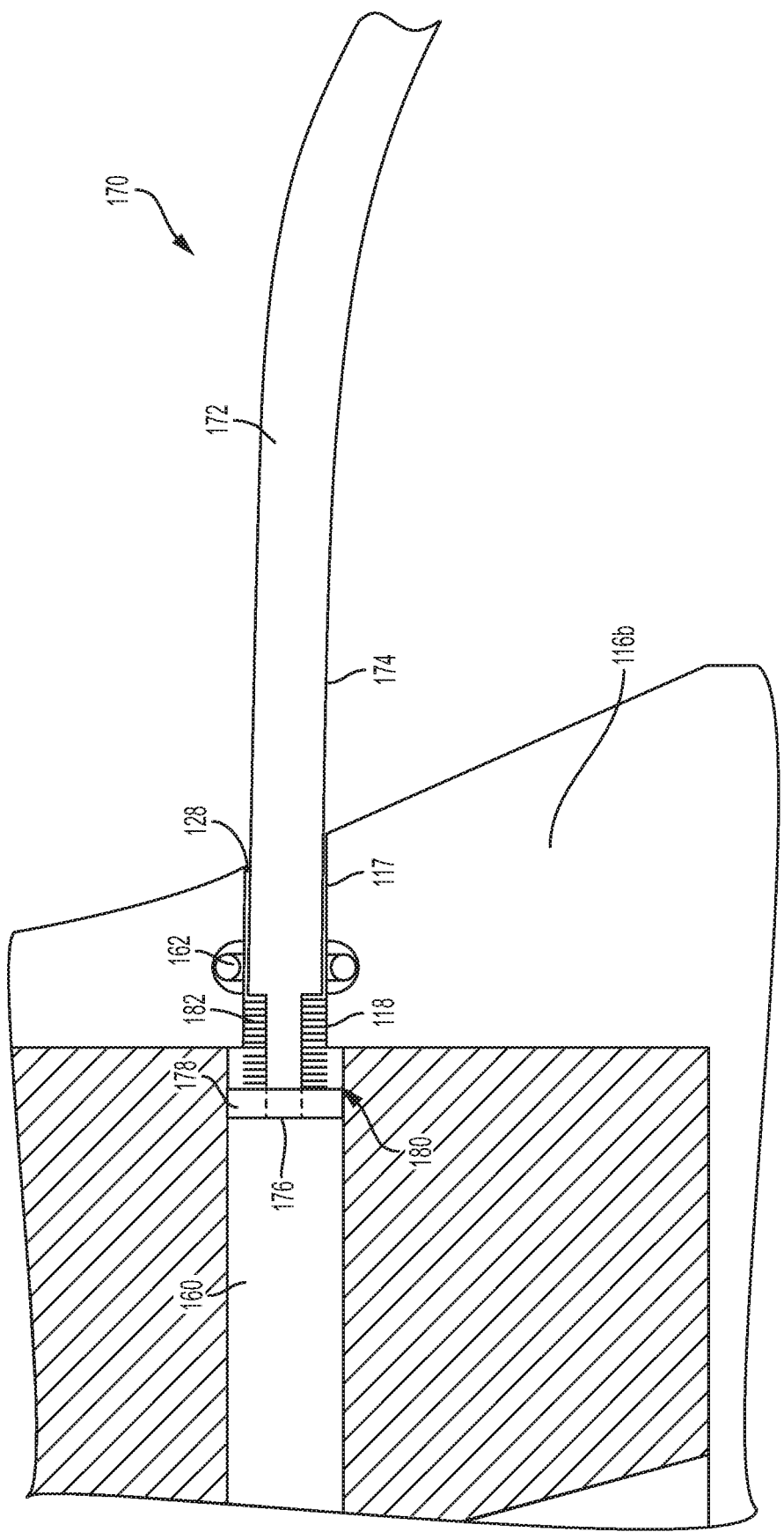
FIG. 3 is a close-up cross-sectional view of the connection formed between the vascular access port and the vascular access catheter of FIG. 1.

Referring now to FIG. 3, in order to inhibit the vascular access catheter 170 from moving proximally into the fluid flow passage 160 (e.g. by fluid pressure of the host 10), particularly after the flange 178 of the vascular access catheter 170 makes contact with shoulder 118 of the vascular access port 110, the proximal end portion 180 of the vascular access catheter 170 may include at least one resilient (deformable) retention element 182 to retain a seated position of the vascular access catheter 170 within the vascular access port 110.

As shown, the proximal end portion 180 of the vascular access catheter 170 includes a plurality of retention elements 182 which are arranged as a series of circular annular deformable retention barbs, which may also be referred to as fins, which each extend continuously around the external perimeter of the tubular body 174 and press against the wall 117 of catheter egress opening 128 formed by sidewall 116b of the cover 116 to provide a friction fit connection. More particularly, the friction fit connection comprises a press-fit connection, formed by the retention elements 182, and more particularly the barbs, deforming against the wall 117 of the catheter egress opening 128 when located therein. The retention barbs may comprise thin ribs formed perpendicular to the longitudinal axis of the tubular body 174. As shown for clarity, only a portion of the retention elements 182 are engaged. Retention elements 182, as well as flange 178 of the vascular access catheter 170 may be formed as a single (monolithic) structure with a remainder of the tubular body 174 of the vascular access catheter 170 or may be made of separate components attached to the tubular body 174, in which case the retention elements 182 and/or flange 178 may be made of a different material from the tubular body 174, such as rigid plastic or metal. The retention elements 182 and/or flange could also be formed as an attached ring to the tubular body 174, which may be threaded or textured.

In the foregoing manner, unlike the positive mechanical connection discussed above, the friction fit connection inhibits the vascular access catheter 170 from being pulled from the vascular access port 110 through the fluid passage access opening 125 until consciously disengaged.

Referring now to FIG. 4, in order to remove and replace vascular access catheter 170 after the vascular access port 110 and the vascular access catheter 170 have been implanted, with the vascular access catheter 170 extending into a blood vessel of the host the implanted vascular access port 110 may be operated such that the needle 121 of the vascular access port 110 penetrates through cutaneous tissue 20 of the host 10 to become exposed above the cutaneous tissue 20.

Thereafter, access to the fluid passage 160 of the vascular access port 110 may be established through fluid passage access opening 125 of the needle 121, particularly by removing removable tip 123 (see FIG. 7) from the shaft 122 of needle 121. As set forth above, the fluid flow passage 160 may be operable to introduce fluid to a host 10 and/or remove fluid from the host 10. Thereafter, a guidewire 200 may be extended into the fluid flow passage 160 as may be taught by the Seldinger technique.

A guidewire 200 may then be extended into the fluid flow passage 160 of the vascular access port 110, through lumen 172 of the vascular access catheter 170, such that they are arranged coxially, and into a lumen 50 of a blood vessel 40 of the host 10, with the distal end 202 of the guidewire 200 being located within the lumen 50 of the blood vessel 40 of host 10. Placement of the guidewire 200 in the lumen 50 of the blood vessel 40 of host 10 may be similar to that taught by the Seldinger technique.

Referring now to FIGS. 4 and 5, after the guidewire 200 is properly positioned, a catheter removal tool 220 may be positioned on the guidewire 200 and used to remove vascular access catheter 170 by introducing the catheter removal tool 220 into the fluid flow passage 160 of the vascular access catheter 170.

As explained in greater detail below, the catheter removal tool 220 is configured to operate with the guidewire 200 and configured to remove the vascular access catheter 170 from the vascular access port 110 through the fluid flow passage 160 and the fluid passage access opening 125 of the vascular access port 110, as well as configured to disengage the mechanical connection between the vascular access catheter 170 and the vascular access port 110, particularly by applying a pulling force to the vascular access catheter 170. In order to achieve such, the catheter removal tool 220 comprises a distal end tip 230 configured to mechanically connect with the proximal end portion 180 of the vascular access catheter 170.

As shown, catheter removal tool 220 comprises a flexible tubular body 222 including a lumen 224. At the distal end portion of the catheter removal tool 220 is located a distal end tip 230 which includes a tip body 232 having a centrally disposed lumen 234 with a distal end opening 236 through which the guidewire 200 extends distally.

Tip body 232 further comprises at least one resilient tip body engagement element 238. Tip body 232 is configured to enter the lumen 172 of the vascular access catheter 170 defined by tubular body 174, and the resilient tip body engagement element 238 is configured to engage with the tubular body 174 of the vascular access catheter 170. As shown, the tip body 232 includes a plurality of engagement elements 238 which are arranged as a series of circular annular engagement barbs, which each extend continuously around the perimeter of the tip body 232 and press against the tubular body 174 of the vascular access catheter 170 to provide a friction fit or other mechanical connection. As shown, the barbs may be formed perpendicular to the longitudinal axis of the tip body 232.

By applying a pushing force to the tubular body 222 of the catheter removal tool 220 adjacent to the entrance of needle 121, the tip body 232 may be forced to enter the lumen 172 of the vascular access catheter 170, and the plurality of engagement elements 238 engage tubular body 174 of the vascular access catheter 170.

Thereafter, by applying a pulling force to the tubular body 222 of the catheter removal tool 220 adjacent to the entrance of needle 121, the retention elements 182 of the vascular access catheter 170 may be disengaged from engagement with the wall 117 of catheter egress opening 128 formed by sidewall 116b of the cover 116 to disengage the mechanical connection there between, particularly as the separation force required to disengage the catheter removal tool 220 from the vascular access catheter 170 is configured to be greater than the separation force required to disengage the vascular access catheter 170 from the cover 116 of the vascular access port 110.

Thereafter, the (occluded) vascular access catheter 170 may be removed from the host 10 through the fluid flow passage 160 of the vascular access port 110 with the catheter removal tool 220, particularly by sliding it axially over and along the guidewire 220, which is held stationary.

After the catheter removal tool 220 and the occluded vascular access catheter 170 are removed from the host 10 by being slid axially along the guidewire 220, the catheter removal tool 220 and the occluded vascular access catheter 170 are removed from the guidewire 220.

Thereafter, a second (unoccluded) vascular access catheter 170 may be positioned on the guidewire 220 with the guidewire 220 within lumen 172 and slid axially along the length of the guidewire 220 to be inserted into the fluid flow passage 160 of the vascular access port 110 through the fluid passage access opening 125. The second vascular access catheter 170 may then follow the guidewire 220 through the tissue 20 of the host 10 and into lumen 50 of blood vessel 40.

Referring now to FIG. 6, in order to properly seat (position) the plurality of retention elements 182 of the vascular access catheter 170 against the wall 117 of catheter egress opening 128 formed by sidewall 116b of the cover 116 of the vascular access port 110, a catheter insertion tool 250 may be positioned on the guidewire 200 proximal to the vascular access catheter 170.

As explained in greater detail below, the catheter insertion tool 250 is configured to operate with the guidewire 200 and configured to insert the vascular access catheter 170 into the vascular access port 110 through the fluid passage access opening 125 and the fluid flow passage 160 of the vascular access port 110, as well as configured to engage a mechanical (friction fit) connection between the vascular access catheter 170 and the vascular access port 110, particularly by applying a pushing force to the vascular access catheter 170.

As shown, the catheter insertion tool 250 may include flexible tubular body 252 including a lumen 254. At the distal end portion of the catheter insertion tool 250 is located a distal end tip 260 which includes a tip body 262 having a centrally disposed lumen 264 with a distal end opening 266 through which the guidewire 200 extends distally.

Tip body 262 further comprises a circular annular flange 268 which has a diameter which is substantially the same as the diameter of flange 178 of the vascular access catheter 170. In this manner, when a pushing force is applied to the tubular body 252 of the catheter insertion tool 250, the circular flange 268 of the tip body 262 pushes against the flange 178 of the vascular access catheter 170 such that the retention elements 182 of the vascular access catheter 170 are properly seated to the cover 116 of the vascular access port 110.

After the vascular access catheter 170 and the catheter insertion tool 250 are introduced into the fluid flow passage 160 of the vascular access port 110, a pushing and/or rotational force may be applied to the tubular body 252 of the catheter insertion tool 250 adjacent to the entrance of needle 121, which will result in flange 268 of the tip body 262 pushing on flange 178 of the vascular access catheter 170. As a result, the proximal end portion 180 of the vascular access catheter 170 may be forced into catheter egress opening 128, such that the plurality of retention elements 182 of the vascular access catheter 170 deform against the wall 117 of catheter egress opening 128 formed by sidewall 116b of the cover 116 of the vascular access port 110 to engage the mechanical (friction fit) connection there between. Thereafter, the catheter insertion tool 250 may be removed from the fluid flow passage 160 of the vascular access port 110, and the guidewire 220 may be removed from the lumen 50 of the blood vessel 40 of the host 10, through lumen 172 of the first vascular access catheter 170 and from the fluid flow passage 160 of the vascular access port 110. After such have been removed, the needle tip 123 may be replaced and the vascular access port 110 may be operated such that the needle 121 of the vascular access port 110 retracts into or below the cutaneous tissue 20 of the host 10.

With regards to extension and retraction of needle 121, as set forth above, FIG. 1 shows movable needle platform 130, and more particularly piston 132, in an extended position in which needle 121 is extended out of the housing 110. In contrast, referring now to FIG. 7, there is shown movable needle platform 130, and more particularly piston 132, in a retracted position in which needle 121 is retracted into the housing 110, and is fully contained within the housing 110.

Movable needle platform 130, as well as piston 132 and needle 121 may be made to extend and retract with use of magnetic forces, in which case as at least a portion of piston 132 comprises a magnetic material, particularly ferromagnetic material, such as iron, nickel and/or cobalt.

As shown in FIG. 7, movable needle platform 130 is made operable by a hand-held actuator 300 which, during use, may overlie the surface 30 of cutaneous (skin) tissue 20 of host 10. More particularly, actuator 300 may include a body 310 which includes a magnet, particularly an electromagnet 314, which may be arranged to operate with an electrical power source, particularly providing direct current to the electromagnet 314.

During use, actuator 300 may be placed over the surface 30 of cutaneous (skin) tissue 20 of host 10, with contact elements 312 in contact with the skin surface 30. Contact elements 312 may be used to space the body 310 and/or electromagnet 314 a short distance from the skin surface, e.g. 1-2 mm.

As shown, the electromagnet 314 comprises at least one electro-magnetic (wire) coil 316, and may comprise a magnetic core 218. Magnetic core 318 may be understood to be a piece of ferromagnetic material (e.g. iron) in the center of the coil 316 which increases the magnetic field. The electric current passed through the coil magnetizes the iron, and the field of the magnetized material adds to the magnetic field produced by the coil 316.

Also as shown, only a portion of the interior of the coil 316 is occupied by the core 318, with the remainder of the unoccupied space creating a recess 320. As explained in greater detail below, recess 320 is to receive needle 121 therein during operation of the actuator 300.

When an electric current of a first polarity is provided to electro-magnet 314, and more particularly electro-magnetic coil 316, coil 316 may emit an electro-magnetic field arranged with a first polarity which attracts the movable needle platform 130, and more particularly the piston 132, to the electro-magnet 314, in which case the movable needle platform 130, and more particularly the piston 132, within housing 112 will be pulled towards the electro-magnet 314 by the force of the electromagnetic field and travel upwards (outwards relative to the host 10) in piston chamber 150.

As the movable needle platform 130/piston 132 travel upwards in piston chamber 150, needle 121 correspondingly extends and passes outwardly through opening 126, at which time the needle 121 continues to travel outwardly and pierces through cutaneous (skin) tissue 20, and more particularly surface 30. The exposed portion of the needle 121 may than enter recess 320 of actuator 300. After the needle 121 has been pulled through cutaneous (skin) tissue 20, actuator 230 may be removed and the needle 121 may be accessed.

As shown, the tip 123 of the needle 121 is designed to operate as a dilator once the distal (terminal) pointed end of the tip 121 (while may be referred to as a pencil tip) has penetrated through the cutaneous (skin) tissue 20. With the configuration as shown, the tip 123 of the needle dilates the tissue 20 rather than cutting through the tissue 20 to minimize injury.

Alternatively, when it becomes desirable to retract the needle 121 back into housing 112, after the tip 123 has been placed on needle 121, an electric current of a second polarity opposite the first polarity (i.e. reverse polarity) is provided to electromagnet 310, and more particularly the electromagnetic coil 316. Coil 316 may then emit an electromagnetic field arranged with a second polarity which repels the movable needle platform 130, and more particularly the piston 132, from the electro-magnet 314, in which case the movable needle platform 130, and more particularly the piston 132, within housing 112 will be pushed away from the electromagnet 314 by the force of the electromagnetic field and travel downwards (inwards relative to the host 10) into the piston chamber 150.

As the movable needle platform 130/piston 132 travel downwards in piston chamber 150, needle 121 correspondingly retracts and withdraws into cutaneous (skin) tissue 20, and more particularly surface 30 and continues to retract through opening 126 and back into chamber 150. After the needle 121 has retracted into housing 112, actuator 300 may be removed.

In another embodiment of the present disclosure, as shown in FIG. 8, the housing 112 may further include a connectable/disconnectable catheter retention member 190 which is detachably connectable to the sidewall 116b of cover 116. As shown, the catheter retention member 190 may comprise a screw thread 192 which threadably engages with a screw thread 194 provided on the sidewall 116 of the cover 116 to connect the catheter retention member 190 to the sidewall 116b of the cover 116 when the catheter retention member 190 is rotated in a first direction (e.g. clockwise) relative to the cover 116. Alternatively, when the catheter retention member 190 is rotated on a second direction opposite of the first direction (e.g. counterclockwise), screw thread 192 threadably disengages from screw thread crew thread 194 provided on the sidewall 116 of the cover 116 to disconnect the catheter retention member 190 from the sidewall 116b of the cover 116. In order to rotate the catheter retention member 190 relative to the housing 112, the catheter retention member 190 may be provided in the form of a connectable/disconnectable stem which extends outward from sidewall 116b of the cover 116. Rotation of the catheter retention member 190 may be better facilitated by extending the catheter retention member 190 from sidewall 116b of the cover 116. To facilitate grasping by hand or a tool such as an open ended wrench, in which the catheter retention member 190 may comprises a hexagonal portion to be gripped by the wrench.

As shown, the catheter egress opening 128 extends through the catheter retention member 190 such that the vascular access catheter 170 may pass through the catheter retention member 190. Similar to the first embodiment, as the tubular body 174 is inserted into fluid flow passage 160 through fluid passage access opening 125, the vascular access catheter 170 may freely extend (pass) through the fluid flow passage 160 and catheter egress opening 128 of the vascular access port 110 until the flange 178 of the vascular access catheter 170 makes contact with shoulder 118 of the vascular access port 110, provided by the catheter retention member 190 of housing 112), which will prevent the vascular access catheter 170 from being removed from the vascular access port 110 through sidewall 116b of cover 116 by virtue of the overlap created between the flange 178 of the vascular access catheter 170 and the shoulder 118 of the vascular access port 110 provided by catheter retention member 190.

However, in contrast to the first embodiment, the embodiment of FIG. 8 permits the vascular access catheter 170 to be separated from the vascular access port 110 without extending needle 121 out from the housing 112 and removing removable tip 123 to gain access to flow passage 160. Thus, if a need arises to replace the vascular access port 110 without replacing the vascular access catheter 170, such may be performed with a minimally invasive procedure where the cutaneous tissue (skin) 20 of the host 10 may be cut through from the surface 30 to access catheter retention member 190. Catheter retention member 190 may then be disconnected from the implanted vascular access port 110, along with implanted vascular access catheter 170. The implanted vascular access port 110 may then be replaced with a new vascular access port 110 without necessarily replacing the vascular access catheter 170, which may become desirable, for example, should the vascular access port 110 have operational difficulties or otherwise need to be replaced.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

What is claimed is:

1. A medical device comprising:
an implantable access port including a fluid passage operable to introduce fluid to a host and/or remove fluid from the host, the fluid passage accessible through a fluid passage access opening; and
a needle configured to penetrate the host, wherein the fluid passage access opening is at an end of the needle and at least a portion of the fluid passage is defined by the needle;
an implantable catheter connectable with the access port, the catheter having a proximal end and a distal end;
wherein the catheter is connectable with the access port by a connection within the access port;
wherein the portion of the fluid passage defined by the needle is defined by a lumen of the needle;
wherein the catheter is insertable into the fluid passage of the access port, including the lumen of the needle, through the fluid passage access opening;
wherein the catheter is advanceable through the fluid passage such that the distal end of the catheter extends from the access port and the proximal end of the catheter is located within the access port;
wherein a proximal end portion of the catheter is connectable with the access port within the fluid passage of the access port and/or within a catheter egress opening of the access port;
and wherein the access port includes a housing;
the housing includes the catheter egress opening;
the housing includes a stem extending outward from a wall of the housing; and
the catheter egress opening is provided in the stem.

2. The device of claim 1 wherein:
the catheter is removable from the fluid passage of the access port through the fluid passage access opening.

3. The device of claim 1 wherein:
the catheter is removable from the lumen of the needle through the fluid passage access opening.

4. The device of claim 1 wherein:
the catheter is connectable with the access port by a mechanical connection.

5. The device of claim 4 wherein:
the mechanical connection comprises at least one of a friction fit connection and a positive mechanical engagement connection.

6. The device of claim 5 wherein:
the positive mechanical engagement connection comprises an interference connection formed by a proximal end portion of the catheter and a portion of the access port.

7. The device of claim 6 wherein:
the interference connection is formed by a flange of the catheter overlapped by a shoulder of the access port.

8. The device of claim 5 wherein:
the friction fit connection comprises a press-fit connection formed by a proximal end portion of the catheter and a portion of the access port.

9. The device of claim 8 wherein:
the press-fit connection is formed by at least one resilient deformable retention element of the catheter deforming against a sidewall of the catheter egress opening when located in the catheter egress opening of the access port.

10. The device of claim 1 wherein:

the catheter comprises a tubular body and a proximal end portion which are insertable into the fluid passage of the access port through the fluid passage access opening; and wherein, when the tubular body and the proximal end portion of the catheter are inserted into the fluid passage of the access port, the tubular body of the catheter extends from the catheter egress opening of the access port while a mechanical interference inhibits the proximal end portion of the catheter from passing through the access port and being removed from the access port through the catheter egress opening.

11. The device of claim 10 wherein:

the fluid passage of the access port has a fluid passage diameter and the catheter egress opening of the access port has a catheter egress opening diameter;

wherein the proximal end portion of the catheter has a diameter smaller than the fluid passage diameter and larger than the catheter egress opening diameter; and wherein the mechanical interference, which inhibits the proximal end portion of the catheter from passing through the access port and being removed from the access port through the catheter egress opening, comprises a region of the proximal end portion of the catheter having a diameter larger than the catheter egress opening diameter.

12. A medical device comprising:

an implantable access port including a fluid passage operable to introduce fluid to a host and/or remove fluid from the host, the fluid passage accessible through a fluid passage access opening;

a needle configured to penetrate the host, wherein at least a portion of the fluid passage is defined by the needle;

an implantable catheter connectable with the access port, the catheter having a proximal end and a distal end;

wherein the catheter is connectable with the access port by a connection within the access port;

wherein the portion of the fluid passage defined by the needle is defined by a lumen of the needle;

wherein the catheter is insertable into the fluid passage of the access port, including the lumen of the needle, through the fluid passage access opening;

wherein the catheter is advanceable through the fluid passage such that the distal end of the catheter extends from the access port and the proximal end of the catheter is located within the access port;

a catheter insertion tool configured to insert the catheter into the access port through the fluid passage access opening and the fluid passage of the access port; and wherein the catheter insertion tool is configured to engage a mechanical connection between the catheter and the access port.

13. The device of claim 12 wherein:

the catheter insertion tool is configured to operate with a guidewire.

14. A method of operating a medical device comprising:

operating an implanted access port and a first catheter connected to the access port and extending into a host such that a needle of the access port penetrates through cutaneous tissue of the host to become exposed above the cutaneous tissue;

establishing access to a fluid passage of the access port through a fluid passage access opening of the needle, the fluid passage operable to introduce fluid to the host and/or remove fluid from the host;

introducing a guidewire into the fluid passage of the access port, through a lumen of the first catheter and into the host;

positioning a catheter removal tool on the guidewire;

introducing the catheter removal tool into the fluid passage of the access port;

engaging the catheter removal tool with the first catheter;

removing the first catheter from the host through the fluid passage of the access port with the catheter removal tool;

removing the catheter removal tool and the first catheter from the guidewire;

positioning a second catheter on the guidewire;

positioning a catheter insertion tool on the guidewire;

introducing the second catheter and the catheter insertion tool into the fluid passage of the access port;

introducing the second catheter into the host such that the second catheter extends from the access port into the host;

removing the catheter insertion tool from the fluid passage of the access port; and removing the guidewire from the host, through a lumen of the second catheter and from the fluid passage of the access port.

15. The method of claim 14 further comprising:

disengaging a mechanical connection between the first catheter and the access port after engaging the first catheter with the catheter removal tool.

16. The method of claim 14 further comprising:

engaging a mechanical connection between the second catheter and the access port after introducing the second catheter into the host.

17. The device of claim 12 wherein:

the catheter insertion tool is configured to apply force to the catheter to engage the mechanical connection between the catheter and the access port.

18. The device of claim 12 wherein:

the mechanical connection comprises at least one of a friction fit connection and a positive mechanical engagement connection.

19. The device of claim 18 wherein:

the mechanical connection comprises the friction fit connection; and the catheter insertion tool is configured to push the catheter to engage the friction fit connection.

20. The device of claim 19 wherein:

the friction fit connection comprises a press fit connection between the proximal end portion of the catheter and a portion of the access port; and the catheter insertion tool is configured to push the catheter to engage the press fit connection between the proximal end portion of the catheter and the portion of the access port.

21. The device of claim 18 wherein:

the mechanical connection comprises the positive mechanical engagement connection; and the catheter insertion tool is configured to push the catheter to engage the positive mechanical engagement connection.

22. The device of claim 21 wherein:

the positive mechanical engagement connection comprises an interference connection between the proximal end portion of the catheter and a portion of the access port; and the catheter insertion tool is configured to push the catheter to engage the interference connection between the proximal end portion of the catheter and the portion of the access port.

* * * * *